(12) United States Patent
Boone

(10) Patent No.: US 9,957,316 B2
(45) Date of Patent: May 1, 2018

(54) WEIGHT LOSS BY INHIBITION OF GASTROKINE

(71) Applicant: THE UNIVERSITY OF CHICAGO, Chicago, IL (US)

(72) Inventor: David Lawrence Boone, Granger, IN (US)

(73) Assignee: LUMEN BIO LLC, South Bend, IN (US)

( * ) Notice: Subject to any disclaimer, the term of this patent is extended or adjusted under 35 U.S.C. 154(b) by 48 days.

(21) Appl. No.: 14/652,488

(22) PCT Filed: Dec. 5, 2013

(86) PCT No.: PCT/US2013/073399
§ 371 (c)(1),
(2) Date: Jun. 16, 2015

(87) PCT Pub. No.: WO2014/099400
PCT Pub. Date: Jun. 26, 2014

(65) Prior Publication Data
US 2015/0329623 A1    Nov. 19, 2015

Related U.S. Application Data

(60) Provisional application No. 61/739,501, filed on Dec. 19, 2012.

(51) Int. Cl.
*A61K 39/00* (2006.01)
*C07K 16/18* (2006.01)
*A01K 67/027* (2006.01)
*C07K 14/47* (2006.01)

(52) U.S. Cl.
CPC .......... *C07K 16/18* (2013.01); *A01K 67/0276* (2013.01); *C07K 14/47* (2013.01); *A01K 2217/075* (2013.01); *A01K 2227/105* (2013.01); *C07K 2317/76* (2013.01)

(58) Field of Classification Search
CPC ............................ C07K 16/18; C07K 2317/76
See application file for complete search history.

(56) References Cited

U.S. PATENT DOCUMENTS

| | | | |
|---|---|---|---|
| 2003/0017548 A1 | 1/2003 | Martin et al. | |
| 2004/0086513 A1* | 5/2004 | Fairbrother | C07K 16/1232 424/169.1 |
| 2005/0031582 A1 | 2/2005 | Toback et al. | |
| 2008/0194479 A1 | 8/2008 | Toback et al. | |
| 2010/0113356 A1 | 5/2010 | Toback et al. | |
| 2011/0245168 A1 | 10/2011 | Toback et al. | |

FOREIGN PATENT DOCUMENTS

| | | |
|---|---|---|
| EP | 1595547 A2 | 11/2005 |
| WO | WO 2012/064146 | 8/2012 |

OTHER PUBLICATIONS

Oien Karin A. et al. "Gastrokine I is abundantly and specifically expressed in superficial gastric epithelium, down-regulated in gastric carcinoma, and shows high evolutionary conservation," J. Pathol. 203:789-797 (2004).
Limaye, Advait et al., "Manipulation of Mouse Embryonic Stem Cells for Knockout Mouse Production," Curr Protoc Cell Biol. Chapter 19:Unit 19.13 19.13.1-24 (2009).
World Intellectual Property Organization, International Bureau, International Search Report for International Patent Application No. PCT/US2013/073399, dated Oct. 16, 2014.
World Intellectual Property Organization, International Bureau, International Preliminary Report on Patentability for International Patent Application No. PCT/US2013/073399, dated Jun. 23, 2015.
International Searching Authority, Written Opinion of the International Searching Authority for International Patent Application No. PCT/US2013/073399, dated Jun. 11, 2014.
Yan Guang-Rong et al., "Proteomics characterization of gastrokine I-induced growth inhibition of gastric cancer cells," Proteomics 11:3657-3664 (2011).
U.C. Davis KOMP Repository, Knockout Mouse Project, Gkn1, at https://www.komp.org/geneinfo.php?geneid=59038 (last visited Aug. 13, 2015).
Wiley Online Library, UNIT 19.13, "Manipulation of Mouse Embryonic Stem Cells for Knockout Mouse Production," published online Sep. 1, 2009, at http://onlinelibrary.wiley.com/doi/10.1002/0471143030.cb1913s44/full (last visited Aug. 13, 2015).
Chen, et al., "AMP-18 facilitates assembly and stabilization of tight junctions to protect the colonic mucosal barrier," Inflamm. Bowel Dis. 18(9):1749-1759 (2012).
Toback, et al., "Peptide fragments of AMP-18, a novel secreted gastric antrum mucosal protein, are mitogenic and motogenic," Am J. Physiol. Gastrointest. Liver Physiol. 285:G344-G353 (2003).
European Patent Office, Extended European Search Report for European Patent Application No. 17183607.5, dated Nov. 17, 2017.
Kim, et al., "Investigating Intestinal Inflammation in DSS-induced Model of IBD," Journal of Visualized Experiments 60:1-6 (2012).
Laroui, et al., "Dextran Sodium Sulfate (DSS) Induces Colitis in Mice by Forming Nano-Lipocomplexes with Medium-Chain-Length Fatty Acids in the Colon," PLoS ONE 7(3):1-12 (2012).

* cited by examiner

*Primary Examiner* — Gyan Chandra

(57) ABSTRACT

Gastrokine-1 (Gkn-1) is a stomach protein that protects the gastrointestinal (GI) tract and has properties to manipulate smooth muscle contraction, prevent NSAID-induced ulceration of the gastrointestinal tract of a mammal, inhibit growth and survival of cancer cells and induce weight loss in a mammal. Previously this protein was designated AMP-18.

13 Claims, 10 Drawing Sheets

WEIGHT LOSS BY INHIBITION OF GASTROKINE

CROSS-REFERENCE TO RELATED PATENT APPLICATIONS

This application is the U.S. national stage entry of International Patent Application No. PCT/US2013/073399, filed Dec. 5, 2013, which claims priority to U.S. Provisional Application No. 61/739,501, filed Dec. 19, 2012, the contents of which applications are incorporated herein by reference in their entirety.

BACKGROUND

Gastrokine-1 (Gkn-1) is a stomach protein that protects the gastrointestinal (GI) tract. Previously this protein was designated AMP-18.

SUMMARY

Gkn-1 knockout mice (Gkn-1−/−) were generated. Recombinant Gkn-1 peptide antibodies were produced to investigate this protein and its role in the health of the gastrointestinal tract (GI) tract. Using these approaches, the following information was obtained about how Gkn-1 works to promote GI health and how Gkn-1 may be manipulated to promote human health.

Investigations revealed that: Gkn-1 is a protein made in the stomach and released into the lumen, but it is not digested in the intestine. Gkn-1 promotes cell function and normal health, probably by direct effects on intestinal epithelial cells and by binding to a microbe(s) in the mucus of the GI tract. Gkn-1 also promotes smooth muscle function and facilitates with muscle motility. Gkn-1 protects against aspirin induced ulceration in the gut.

BRIEF DESCRIPTION OF THE DRAWINGS

FIG. 5(A) Gkn-1 staining (bright areas, also shown as arrows) brightly labels a particle that appears to be a microbe in the stomach, suggesting that Gkn-1 was coating microbes and affecting their survival. Examining the mucus of the colon revealed many of these Gkn-1 positive elements suggesting microbes in the outer mucus layer. FIG. 5(B) Immunohistochemistry from colons of conventionally housed mice, which have microbes colonizing the gut, were compared to germ-free mice, which have no microbes in the gut. Mucus staining is shown in the left panels (bright areas, also shown as arrows) and Gkn-1 staining is shown in the right panels (bright areas, also shown as arrows). The outer mucus layer of normal mice displays extensive punctate staining in the outer mucus layer, which is not seen in the outer mucus layer of germ-free mice. These results support a conclusion that Gkn-1 engulfs microbes in the GI tract.

FIG. 6 shows Gkn-1 decorates particles in the lumen of the gut that appear to be microbes. This high magnification image was taken from a histological section of the proximal gut immuno-stained with anti-Gkn-1 antibody (bright areas, also shown as an arrow). The staining clearly defines the outlines of bacteria-shaped objects in the gut. Gkn-1 may be promoting health by binding to and altering survival of microbes in the mucus layers of the colon. Gkn-1 is likely a new type of antimicrobial agent, or an agent that helps a subset of beneficial microbes survive.

FIG. 7. shows representative images from WTR mouse colons stained for Gkn-1 that decorates the inner mucus layer (1) of the small intestine and the outer mucus layer (2) of the colon. The localization of Gkn-1 (bright areas, also shown as arrows) by immunohistochemistry is shown in histological sections from the colon at lower (left panels) and higher (right panels) magnification. The "inner mucus layer" (1) indicates the sterile inner mucus layer in the lumen of the intestine. The "outer mucus layer" (2) indicates the outer mucus layer, which is suffused with microbes and stains very brightly for Gkn-1 (bright areas, also shown as arrows).

FIG. 8. shows Gkn-1 decorated microbes are rod shaped.

DETAILED DESCRIPTION

Gkn-1 is Made in the Stomach but Traverses the GI Tract

Figure 1:
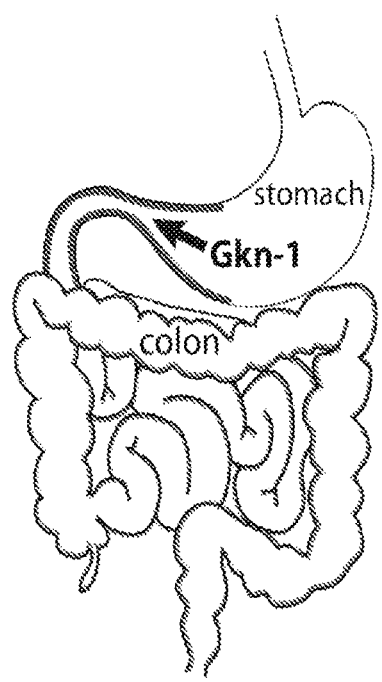
FIG. 1. Gkn-1 is made exclusively in the stomach and is secreted into the mucus. Gkn-1 traverses the GI tract and acts to promote colon health.

Using PCR (measurement of gene expression in tissues) and immunolocalization (staining with an antibody to detect localization of a protein in a tissue) it was shown that Gkn-1 is made by epithelial cells of the stomach. The protein has not been found to be made anywhere else and is secreted into the lumen of the stomach. Gkn-1 can traverse the entire length of the gastrointestinal (GI) tract, from the stomach into the duodenum, along the small bowel (jejunem and ileum) and into the colon, and may do so within the mucus layer of the intestine, which lines the entire GI tract and moves along the GI tract in the same manner as food does (FIG. 1).

Figure 2:
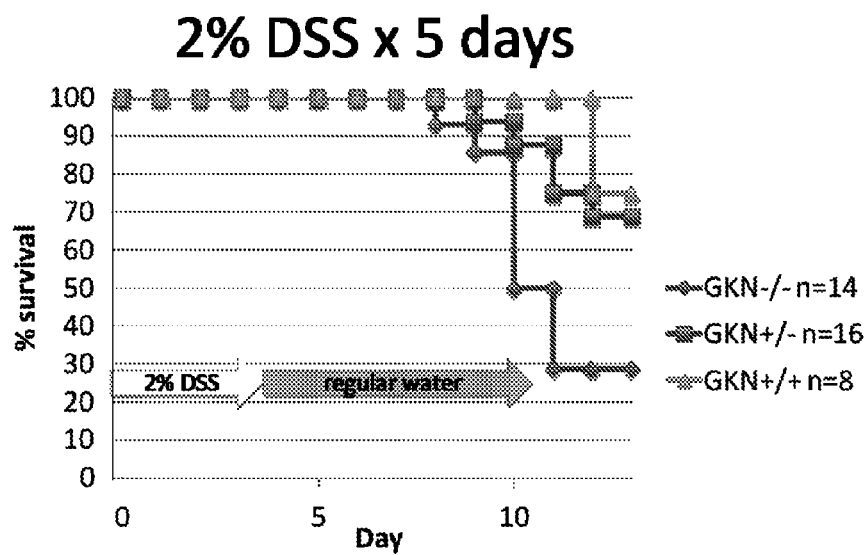
FIG. 2. Mice were treated with 2% Dextran sulfate sodium (DSS) in drinking water for 3 days which causes colonic epithelial cell apoptosis, leading to inflammation. Survival curve of mice (top panel) shows that Gkn-1 is essential for protection from this type of intestinal damage. Gkn-1 protects against DSS-induced epithelial cell death in the colon which was measured by TUNEL staining (bright areas, also shown as arrows) of histological sections (bottom panel). Gkn-1−/− mice displayed extensive epithelial cell death compared to Gkn-1+/− mice.
Figure 2:
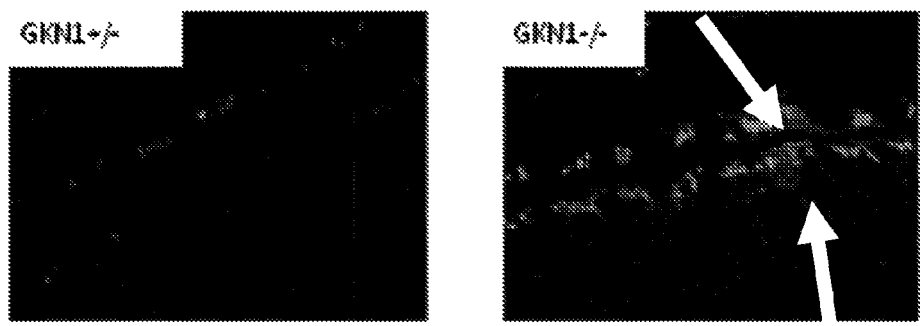
Figure 4:
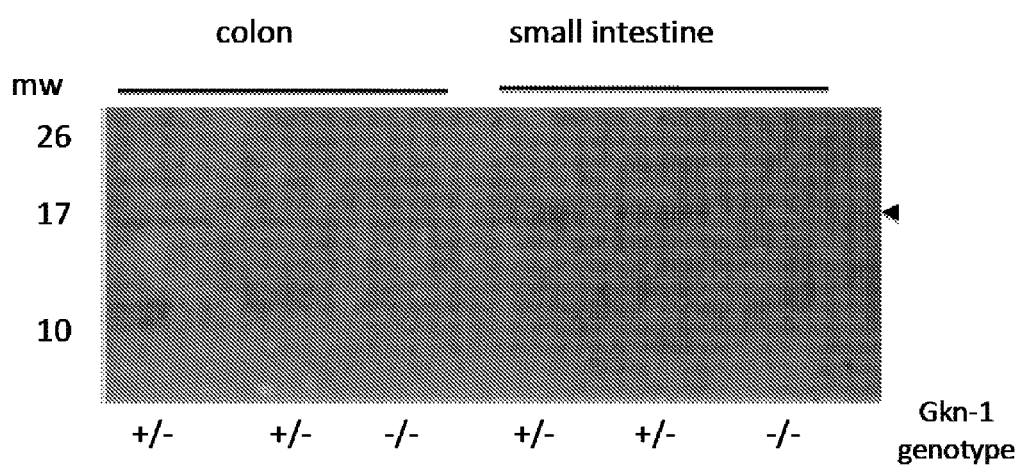
FIG. 4. Gkn-1 protein levels in the mucus of the colon and small intestine. Mucus proteins were isolated by shaking intestinal pieces in PBS and collected by acetone precipitation, followed by immunoblotting with anti-Gkn-1 antibody. Arrowhead indicates predicted Gkn-1 band. This immunoblot shows that full length Gkn-1 can be identified in the mucus of the small and large intestine, supporting that it traverses the GI tract intact.
Figure 5:
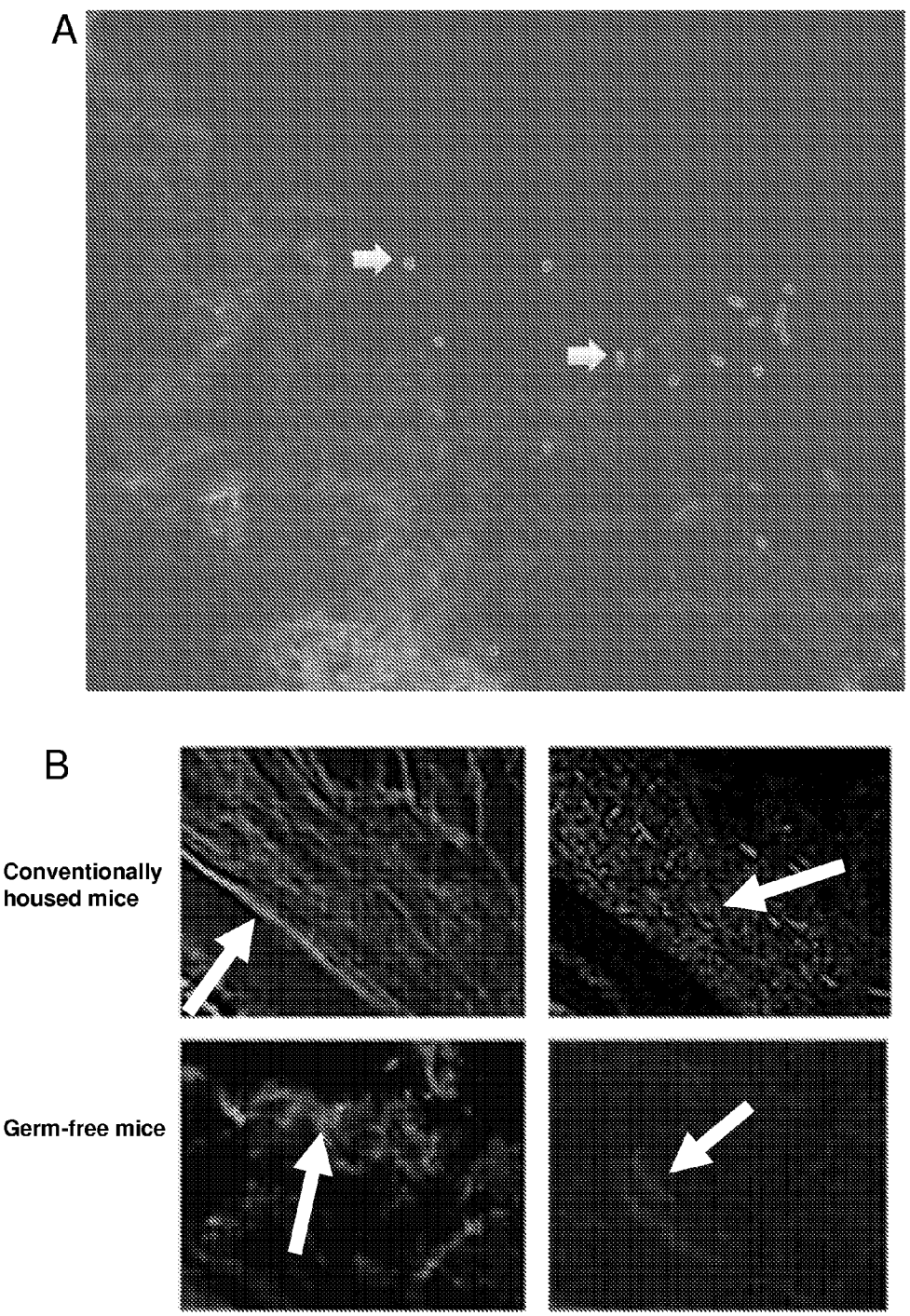
FIGS. 5-8 show immunolocalization of Gkn-1 in normal mice.
Figure 6:
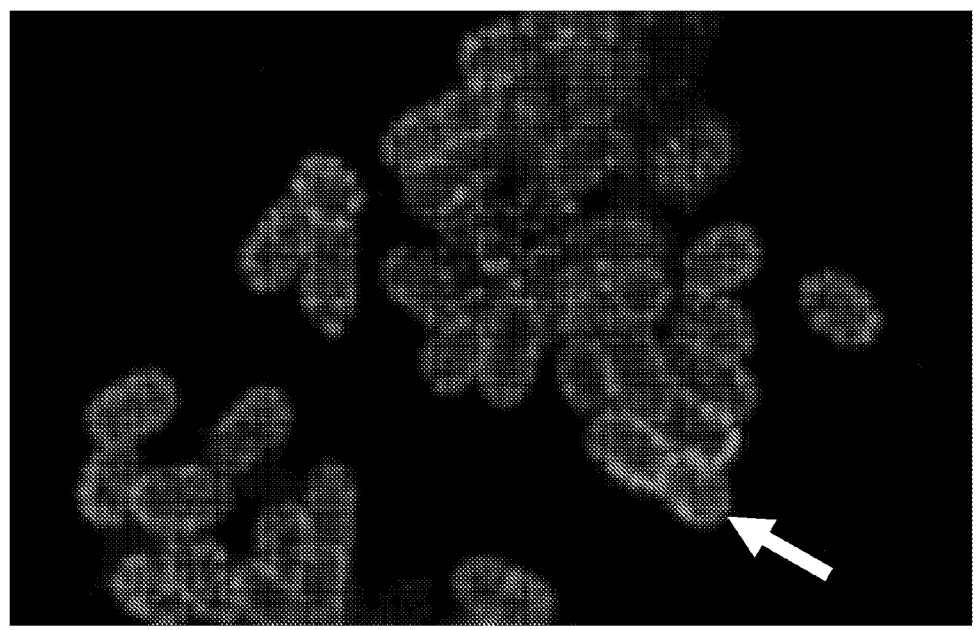
Figure 10:
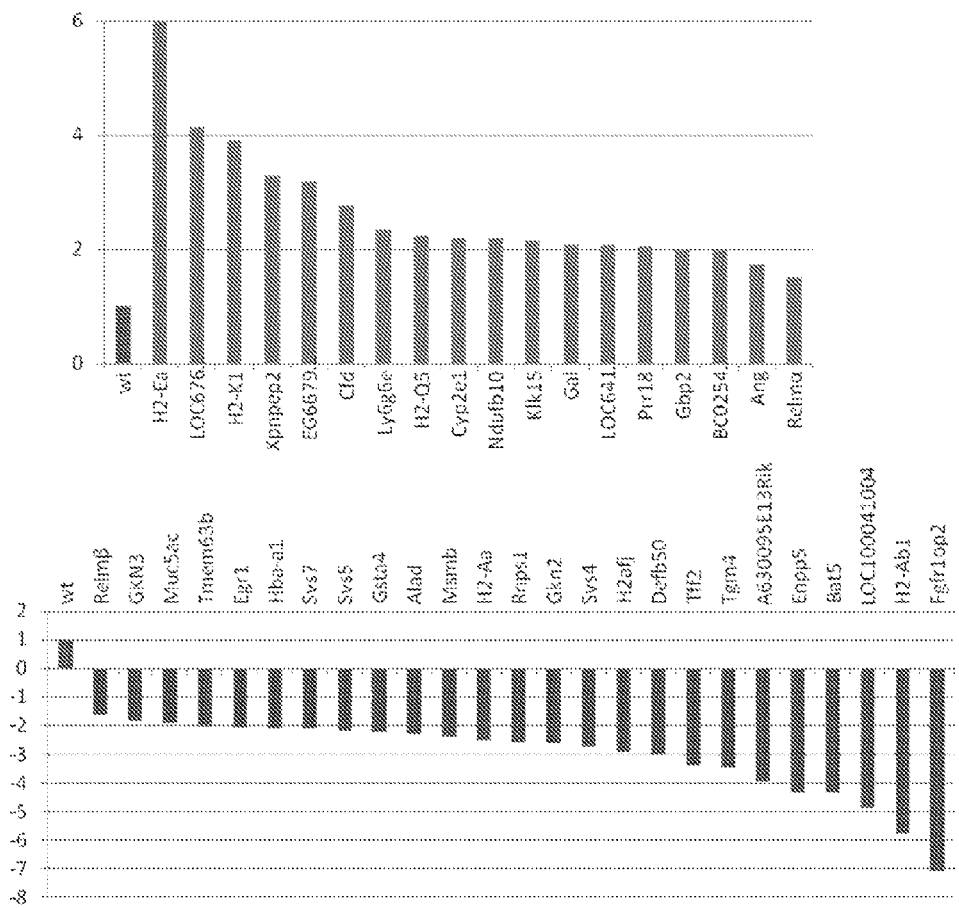
FIG. 10. Altered gene expression in the colon of Gkn-1−/− mice. Gene expression microarrays were performed on RNA extracted from untreated WT and Gkn-1−/− colons. The results show a select number of genes that were expressed at higher levels in Gkn-1−/− mice (upper panel) compared to WT mice, or genes expressed at lower levels in Gkn-1−/− mice (lower panel).

Support for the conclusion that Gkn-1 traverses the entire GI tract was generated from the following studies: (1) PCR performed on specimens collected from human and mouse small bowel and colon in which gene expression was only observed in the colon. (2) Gkn-1−/− mice were generated and their colon tissue analyzed for gene expression changes compared to Gkn-1+/− or Gkn-1+/+ (wild-type) mice; it was found that many genes had altered expression in the colons of Gkn-1−/− mice. This suggested that Gkn-1 was having an effect on the colon, even though it was only made in the stomach (FIG. 10). (3) Gkn-1−/− and Gkn-1+/+ mice were challenged with DSS, a compound that causes inflammation in the colon; it was found that Gkn-1−/− mice were exquisitely sensitive to this challenge, indicating that Gkn-1 normally protects the colon from this type of injury (FIG. 2). (4) Mucus proteins were isolated from the small bowel of Gkn-1+/+ and Gkn-1−/− mice and immunoblotting was performed on these extracts. This showed that full length (18 kDa) Gkn-1 protein could be extracted from the mucus layer of the small bowel and the colon (FIG. 4). Together these studies showed that Gkn-1 is required to protect the colon from injury and that Gkn-1 may do this by traversing the GI tract from the stomach to the colon. This suggests that Gkn-1 could be delivered orally (i.e. eaten, as a food) and benefit patients with inflammation along the GI tract.

Potential Uses of Anti-Gkn-1 Antibodies

An antibody that binds and inhibits the action of Gkn-1 is useful for weight loss. Conversely an antibody designed to bind, stabilize and enhance the activity of Gkn-1, provides protection from colonic inflammation, protection from NSAID induced inflammation, promotes intestinal motility and improved weight gain.

Mechanisms of Action of Gkn-1

Previous studies using cell cultures have concluded that Gkn-1 acts directly on intestinal epithelial cells (IEC). This effect may include promotion of IEC proliferation and migration, which would explain how Gkn-1 protects the gut from injury. It is also known that Gkn-1 promotes tight junctions between IEC to improve the intestinal barrier. Disclosed herein are results showing that Gkn-1−/− mice display rapid IEC death when challenged with DSS, indicating that Gkn-1 protects IEC from cell death (FIG. 2). All or any of these effects may account for the beneficial effects of Gkn-1 in the GI tract.

Gkn-1 and Gastric Cancer

Gastric cancer is one of the most common and deadly forms of cancer in the world. It has been observed that gastric cancers lose expression of Gkn-1. Some have suggested that loss of Gkn-1 expression leads to gastric cancer. Countering this concept are present results that gastric cancer has not been observed in Gkn-1−/− mice, therefore loss of Gkn-1 is not shown to cause gastric cancer. Conversely, gastric cancers inhibit the expression of Gkn-1 in order to grow and survive. Therefore treatment with Gkn-1 may be an effective pathway to suppress or kill gastric cancer, or cells that have metastasized from gastric cancers to other sites in the body.

Other Indications

Oral Mucositis: this is a painful condition that can occur upon radiation or chemotherapy treatment of the head and neck (for cancer). Expression of Fgfr1op2, a protein involved in wound healing, is dramatically reduced in Gkn-1−/− mice, indicating that Gkn-1 may be important in wound healing (FIG. 10). Thus, Gkn-1 may be useful in the treatment or prevention of oral mucositis. Recombinant Gkn-1 or anti-Gkn-1 antibody could be used in a mouthwash formulation to treat or prevent oral mucositis.

Necrotizing Enterocolitis (Nec): This condition is prevalent in premature infants and results in the destruction of the gut lining, typically the distal portion of the small bowel. The cause is not clear but involves the intestinal microbiota, a failure to heal mucosal injury and increased intestinal epithelial cell death. Because Gkn-1 can alter the intestinal microbiota, decrease intestinal epithelial cell death, and can improve wound healing or inflammatory bowel disease, treatment with Gkn-1 or Gkn-1 antibody may be useful for the treatment of NEC.

Postoperative ileus: Following surgery the intestine can become "paralyzed" in that the normal peristaltic and other movement of the intestine is stopped. This is a major and common complication following surgery, even outside the abdomen. It can be dangerous depending on its duration and severity. Because Gkn-1 alters (manipulates) intestinal motility, as shown in Example 2, Gkn-1 or Gkn-1 antibody may be used to treat post-operative ileus.

Disorders of gut discontinuity: The gut is essentially a continuous tube with the stomach near the front end. Gkn-1 is made in the stomach and coats the entire GI tract left beneficial effects along the length of the gut. In cases where the gut is not a continuous tube, such as following bariatric surgery, ileostomies to rest the colon or ileostomies to rest the distal portion of the small bowel following ileo-anal anastomosis procedures, the portion of the gut not in luminal continuity with the stomach will be deprived of Gkn-1. This may be why these tissues often display altered physiology or bacterial overgrowth. Gkn-1 or Gkn-1 antibody administered to the lumens of these discontinuous areas, may improve healing and restoration of normal function.

Gkn-1 as a Biomarker

Gkn-1 is made in the stomach and secreted into the gut lumen where it appears to be very stable and traverses the GI tract intact. It does not get secreted into the blood circulation from the stomach under normal conditions. Thus, if Gkn-1 appears in the blood it is there because it has leaked into the bloodstream following damage or alteration of the gut lining. Thus, measurement of Gkn-1 in the blood may be used as a biomarker for altered gut permeability which is the result of, or indicative of: Crohn's disease, ulcerative colitis, celiac disease, IBS, intestinal cancer and so on. In healthy individuals there should be no, or very low, Gkn-1 in the blood. In unhealthy individuals, Gkn-1 is present in the blood at higher levels. This is assessed by an ELISA or other blood assay to diagnose occult barrier loss in the GI tract.

GKN-1 as a Label for Bacteria

Gkn-1 decorates bacteria in the gut lumen (FIGS. 5-8). This indicates that Gkn-1 is killing or protecting intestinal bacteria, or that it is simply binding to some type of microbe in the gut. Gkn-1 labeled with a fluorescent tag, or Gkn-1 labeled with antibodies, allows identification of subsets of bacteria based on their binding to Gkn-1.

Gkn-1 Peptides or Pig Mucus

Significant beneficial effects of a peptide derived from full length Gkn-1 have been reported. [LDALVKEKKLQGKG-PGGPPPK (SEQ ID NO: 1), SEQ ID NO: 12 in U.S. Pat. No. 8,278,269]. This peptide, or full length Gkn-1 is made in *E. coli*, and may be used to produce the beneficial effects of Gkn-1. Also, Gkn-1 may be produced in human cell lines (HeLa, HEK293 etc.). In addition, because Gkn-1 is produced in large quantities in the stomach. Gkn-1 may be isolated from the stomach mucus of farm animals, such as pigs, which have a stomach similar to mammals. All of these preparations may be dried and fed directly to persons in need thereof, or encapsulated in gelatin and fed in that manner.

Gkn-1 as a Food Supplement

Gkn-1 is made and released into the stomach, and is a very stable protein. To obtain the benefits conferred by endogenous Gkn-1, a mammal could eat unaltered Gkn-1. Alternatively, Gkn-1 may be added as a dried powder to a liquid or solid food and consumed. Gkn-1 may be encapsulated in gelatin to allow it to bypass the stomach acid. Gkn-1 may be obtained from transgenic sheep; goats or cows could be made that secrete Gkn-1 in their milk and would allow Gkn-1 to be consumed in any dairy products derived from these sources. These approaches relate to Gkn-1 peptides, recombinant Gkn-1, or Gkn-1 derived from pig stomach mucus. If the benefit of Gkn-1 manipulation is achieved through the use of a Gkn-1 antibody, chickens are inoculated with Gkn-1. The eggs or egg meal are a source of the antibody, because chickens deposit antibodies in their eggs. The eggs would therefore contain anti-Gkn-1 antibody.

EXAMPLES

Example 1: Gkn-1 Protects Against NSAID-Induced Ulceration and Inflammation

Figure 9:
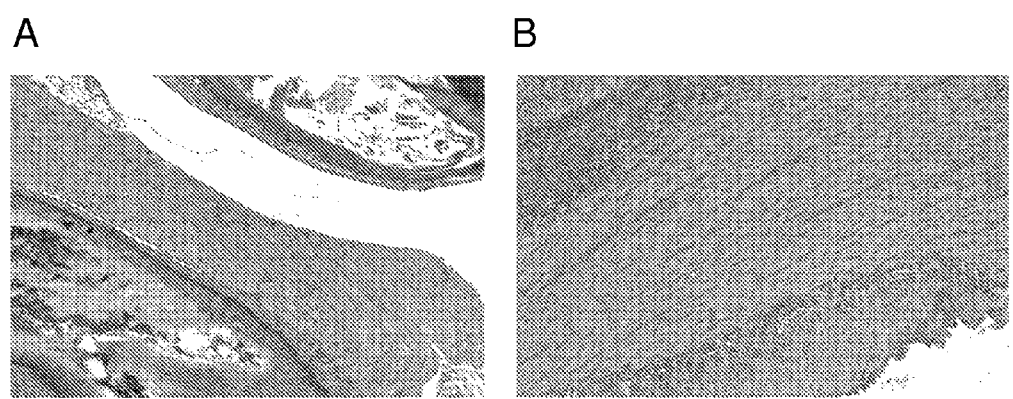
FIG. 9. demonstrates Gkn-1 is essential for protecting the gut from NSAIDs. (A) The WT and (B) Gkn-1−/− mice were fed peroxicam (an NSAID like aspirin) over three days, a treatment which normally is done over a prolonged period of time, and their stomach tissue was collected for histology. WT mice showed some minor inflammation here and there, but the Gkn-1−/− mice had high levels of inflammation throughout the lining of the stomach, including in the mucosa and muscle tissue. All the Gkn-1−/− mice died within a week from perforations in their GI tract.

NSAIDs are used widely for their pain and anti-inflammatory benefits, but these drugs can have side effects ranging from upset stomach to life threatening gastrointestinal ulceration and bleeding. Common NSAIDs include aspirin, ibuprofen and many others. It is reported that NSAIDs causes the loss of Gkn-1 expression in the stomach. The relationship between Gkn-1 and NSAID induced ulceration and inflammation was examined by using Gkn-1−/− mice. Mice were fed the NSAID peroxicam for 7 days, and all of the Gkn-1−/− mice died from ulceration, whereas the Gkn-1+/+ mice survived. The duration of peroxicam exposure was shortened to three days and it was found that Gkn-1−/− mice developed extensive inflammation in the stomach and small bowel, whereas Gkn-1+/+ mice did not (FIG. 9). These results indicate that Gkn-1 is important for protection from NSAID induced intestinal injury. Gkn-1 can be taken orally by patients taking NSAIDs in order to decrease the unwanted GI complications of NSAID use.

Example 2: Gkn-1 Promotes Intestinal Motility

To create more Gkn-1−/− mice, Gkn-1−/− males were mated to Gkn-1−/− females. These breedings produced no litters, whereas breeding Gkn-1−/− males to Gkn-1 +/− females produced the normal complement of litters. This suggested that expression of Gkn-1 in the female is important for reproduction. To better understand this, the Gkn-1−/− females were examined throughout pregnancy. These females become pregnant and the pups developed normally until the final day of gestation, when parturition should occur. At that point, when a normal female would deliver her pups, the Gkn-1−/− female did not. Based on these results, the conclusion is Gkn-1 plays a role in smooth muscle contraction, because smooth muscle contraction in the uterus is a key step in parturition. Smooth muscle also plays many essential roles in the gut, from emptying of the stomach to the normal process of pushing the food along the gut, and finally to defecation. Disorders of smooth muscle function in the gut range from rare fatal disorders to less severe but extremely common disorders, for example, irritable bowel syndrome (IBS) and gastroesophogeal reflux disorder (GERD). Gkn-1 may function to improve or maintain efficient smooth muscle contraction. Treating mammals that have IBS, GERD or other disorders of intestinal motility, is by administration Gkn-1. A suitable route of administration is oral.

Example 3: Gkn-1 Promotes Weight Gain

Gkn-1−/− mice in a normal unchallenged setting do not develop inflammation or other overt diseases. However, Gkn-1−/− mice are consistently of a lower body weight than their age and sex matched Gkn-1+/− or Gkn-1+/+ littermates. This suggests that Gkn-1 supports weight gain in unmanipulated mice. Conversely, a lack of Gkn-1 should promote weight loss. Gkn-1 taken as a food supplement may improve weight gain in patients who need to do so, including short gut patients and the elderly. Other uses for improved weight gain include the agricultural need to have mammals gain more weight from the food they eat.

Obesity is a growing problem with serious health, economic and public policy implications. Therefore inhibition of Gkn-1 may be an important avenue for weight loss. A Gkn-1 antibody that binds and inhibits Gkn-1 in the GI tract is prepared by methods known in the art contemplated to promote weight loss. An antibody to Gkn-1 may be delivered in food, such as eggs from chickens. Administration of the eggs, or other preparations of Gkn-1 antibodies, would lead to weight loss.

Example 4: Mechanisms of Action of Gkn-1

Using Gkn-1−/− mice, another mechanism was identified that would account for Gkn-1 effects. Gkn-1 decorates microbes in the lumen of the GI tract (FIGS. 5-8). This may alter the intestinal microbial community, a process that could explain some or all of the biological effects observed in Gkn-1−/− mice. Gkn-1 may have antibiotic effects on a subset of microbes, or protect a helpful subset of microbes (probiotic effects). Thus Gkn-1 is used useful for the control of the gut microbiota, either as an antibiotic or probiotic factor. Mammals are treated with pro or anti-Gkn-1 therapies to affect their gut microbiota in helpful ways that could affect any of the processes described above. Finally, because Gkn-1 expression is lost during *H. pylori* infection and therefore Gkn-1 and/or an antibody to stabilize Gkn-1 is a therapy for the treatment of *H. pylori* infection.

Figure 3:
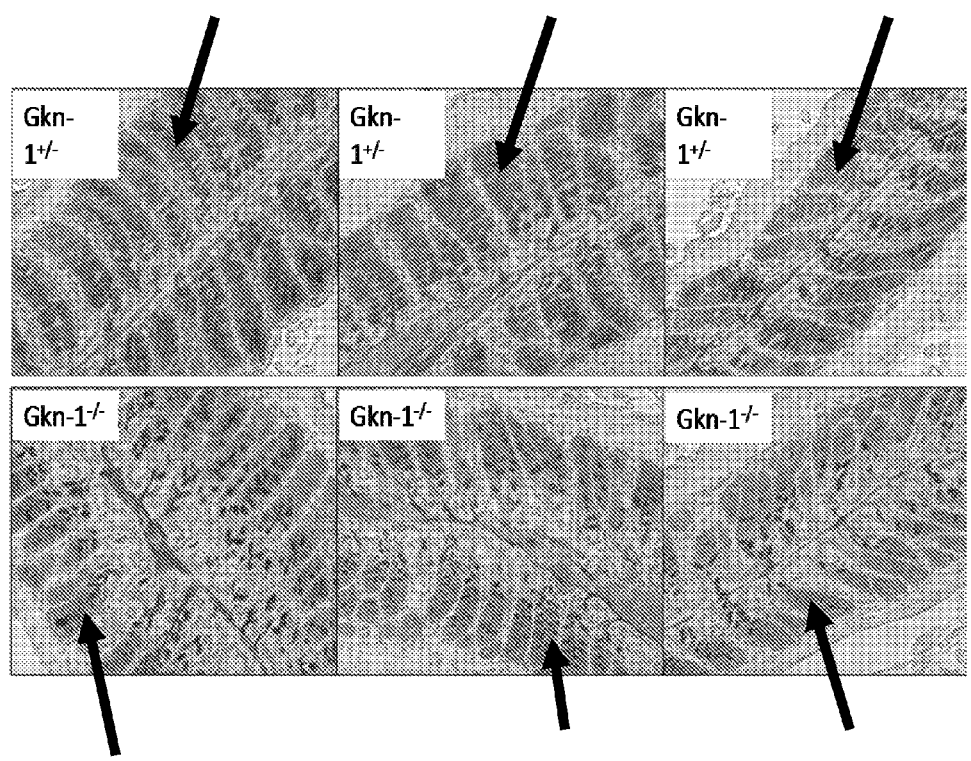
FIG. 3. Alcian blue-stained (dark areas, also shown as arrows) histological sections from colons of six (3 Gkn-1+/− and 3 Gkn-1−/−) mice showing altered goblet cell phenotype in Gkn-1−/− mice.

Mice in FIG. 3 were not manipulated in any way. The data shows that goblet cell morphology and/or number were altered in the colons of mice lacking Gkn-1. This may be a direct effect of Gkn-1 on goblet cells, or an indirect effect of Gkn-1 on immune or other cells, or an effect of Gkn-1 on the microbiome, leading to the altered goblet cell phenotype.

Example 5: Gkn-1 as a Label for Bacteria

Figure 7:
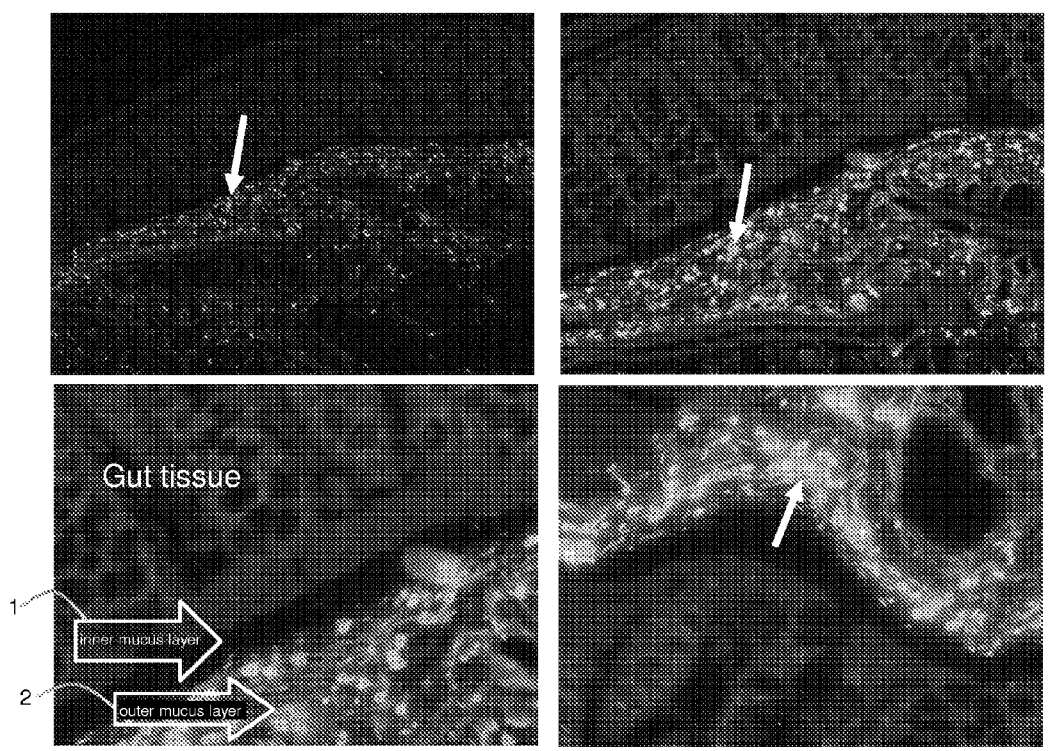
Figure 8:
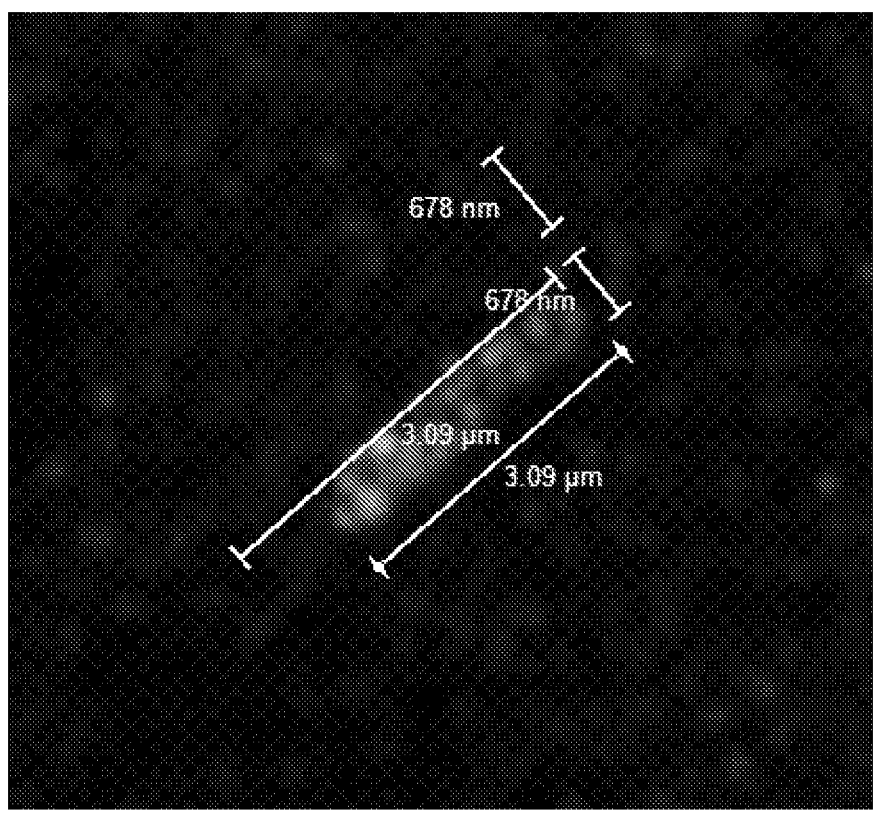

FIGS. 5 to 8 show immunolocalization of Gkn-1 in normal mice. Gkn-1 staining (bright areas, also shown as arrows) was brightly labeling a microbe-like particle in the stomach, which suggests that Gkn-1 was coating these microbes and affecting their survival. Mucus of the colon was decorated with Gkn-1 and many Gkn-1 positive microbe-like elements were found in the outer mucus layer (FIG. 7).

Gkn-1 is used to promote health, by binding to and altering survival of microbes in the mucus layers of the colon. Gkn-1 may be a new type of antimicrobial agent, or something that helps a subset of beneficial microbes to survive.

Materials and Methods

Generation of Gkn-1−/− Mice

Targeted embryonic stem cells were derived by the Knockout Mouse Consortium as described by Limaye et al. (2009) (https://www.komp.org/geneinfo.php?geneid=59038) and delivered to blastocysts as described (http://onlinelibrary.wiley.com/doi/10.1002/0471143030.cb1913s44/full). Chimera were selected and bred to C57Bl/6 mice and offspring were screened for the transmission of the gene-targeted allele. Mice heterozygous for the deletion of Gkn-1 (Gkn-1 +/−) were selected and bred to C57B1/6 mice to establish a colony of gene-targeted mice. To generate Gkn-1−/− mice, Gkn-1+/− females were bred to Gkn-1+/− males and offspring were assessed for Gkn-1 deletion by PCR primers directed across the Gkn-1 allele.

All mice were fed ad libitum and monitored for health daily and body weight weekly, and all breeding and experimental protocols were approved by the University of Chicago Institutional Animal Care and Use Committee (protocols #71661, #72089).

DSS Colitis Model of IBD (IBS)

For acute DSS-colitis studies, groups of 4-6 mice were fed DSS (2% w/vol in water) (MW 36,000-50,000, MP Biosciences) ad libitum for 5 days, then returned to regular drinking water for recovery and euthanized on the days indicated in the results. Mouse weight and disease activity index (DAI) were recorded blindly for the duration of the DSS cycle, and occurrences of euthanasia resulting from mice exceeding IACUC approved endpoints (weight loss exceeding 20% of maximum body weight, persistent positive fecal blood test or rectal bleeding, hunched posture, rectal prolapse) were recorded as the percentage of survival for these experiments. The DAI score was calculated by averaging the scores of weight loss, stool consistency, and rectal bleeding (0=healthy, 4=maximum colitis). For weight, no weight loss was scored as 0, weight loss of 1-5% from baseline as 1, 5-10% as 2, 10-15% as 3, and >15% as 4. Fecal blood was determined with hemoccult cards (Beckman Coulter). For bleeding, no blood was scored as 0, hemoccult positive stool as 2, and gross rectal bleeding as 4. For stool consistency, normal, well-formed pellets were scored as 0, pasty and semi-formed stool as 2, and liquid stool or diarrhea as 4. Colons were excised and measured for length analysis. For histological analysis, colons were fixed in 10% formalin and paraffin embedded in longitudinal sections. Sections (5 μm) were stained with hematoxylin and eosin and scored by a pathologist blinded to the genotype using the following criteria: (0) histologically normal; (1) crypt architectural distortion or increased lamina propria lymphocytes, but no increase in granulocytes; (2) lamina propria granulocytes are increased, but intraepithelial granulocytes are absent; (3) intraepithelial granulocytes are present, no crypt abscesses; (4) crypt abscesses present in fewer than 50% of crypts; (5) crypt abscesses present in greater than 50% of crypts or erosions are present.

Peroxicam Model of Intestinal Ulceration

Peroxicam at 200 ppm was mixed geometrically with NIH-31M powdered chow (Harland-Tekland, Indianapolis, Ind.) and fed to the mice for 3-10 days. Mice were monitored for health as described above for the DSS model of colitis.

Immunohistochemistry and Histology

Immunohistochemistry was performed on frozen intestinal sections (5 μm) embedded in O.C.T. Compound (Sakura Finetek, Torrance, Calif.). Samples were hydrated via successive PBS washes and blocked with 5% BSA in a humidified chamber (45 minutes, 20° C.) before incubation with primary antibodies (0.4 μg/ml-2 μg/ml in 2.5% BSA, 18 h, 4° C.). Samples were washed the following day with PBS, incubated with fluorescent secondary antibody (0.1 μg/ml in PBS) and Hoechst stain (2 μg/ml). Stained samples were mounted in ProLong Antifade (Invitrogen) and photographed using a fluorescence microscope (DM2500, Leica Microsystems, Buffalo Grove, Ill.). In some cases samples were fixed in Carnoys, processed and embedded in paraffin. Immunohistochemistry of these samples was performed as described above following deparrifinization and hydration of the tissue.

For standard histology using Hematoxylin & Eosin, or Alcian Blue staining, specimens were fixed in formalin, embedded in Parraffin, sectioned at 5 uM, processed and hydrated to PBS and then stained mounted and photographed by light microscopy.

Immunoblotting (Westerns)

Proteins were isolated from intestinal mucus collected by repeated washing in PBS followed by acetone precipitation and rehydration in SDS Laemmli buffer. Proteins were resolved by SDS-PAGE (4-12% Bis-Tris NuPAGE acrylamide gel from Invitrogen) and transferred to polyvinylidene fluoride (PVDF) membranes (Millipore, Billerica, Mass.) using NuPAGE transfer buffer and an XCell-II blot module (Invitrogen), and then immunoblotted with the indicated primary antibodies. Fluorescent-labeled secondary antibodies were then applied and the blots were visualized using the Odyssey Imaging System (LI-COR Biosciences, Lincoln, Nebr.).

PUBLICATIONS

Limaye, A. et al. (2009) *Current Protocols in Cell Biology*, 19.13.1-19.13.24

Oien et al. (2004) *J. Pathol.* 2004 July; 203(3):789-97

The invention claimed is:

1. A method to promote weight loss in a mammal, the method comprising administering an agent to the mammal, wherein the agent inhibits the action of Gkn-1 in the mammal, wherein the agent is an antibody or immunoglobulin, wherein the mammal does not have colitis, and wherein the agent inhibits the action of Gkn-1 in the mammal by binding to and neutralizing Gkn-1 in the mammal, thereby promoting weight loss in the mammal.

2. The method of claim 1, wherein the antibody or immunoglobulin.

3. The method of claim 2, wherein the chicken antibody or immunoglobulin is obtained from one or more chickens inoculated with Gkn-1.

4. The method of claim 3, wherein the chicken antibody or immunoglobulin is obtained from one or more eggs of the one or more chickens inoculated with Gkn-1.

5. The method of claim 4, wherein the chicken antibody or immunoglobulin is of the isotype Immunoglobulin Y (IgY).

6. The method of claim 5, wherein the mammal consumes the egg and wherein the chicken antibody or immunoglobulin of isotype IgY passes into the distal gut of the mammal and binds to and neutralizes the Gkn-1 inside the mammal.

7. An agent that inhibits the action of Gkn-1, wherein the agent, when administered to a mammal, promotes weight loss, wherein the agent is an antibody or immunoglobulin, wherein the mammal does not have colitis, and wherein the agent inhibits the action of Gkn-1 in the mammal by binding to and neutralizing the Gkn-1 in the mammal.

8. The agent of claim 7, wherein the antibody or immunoglobulin is a chicken antibody or immunoglobulin.

9. The agent of claim 8, wherein the chicken antibody or immunoglobulin is obtained from one or more chickens inoculated with Gkn-1.

10. The agent of claim 9, wherein the chicken antibody or immunoglobulin is obtained from one or more eggs of the one or more chickens inoculated with Gkn-1.

11. The agent of claim 10, wherein the chicken antibody or immunoglobulin is of the isotype Immunoglobulin Y (IgY).

12. The agent of claim 11, wherein the mammal consumes the egg and wherein the chicken antibody or immunoglobulin of isotype IgY, passes into the distal gut of the mammal and binds to and neutralizes the Gkn-1 inside the mammal.

13. A method for promoting weight loss in a mammal, wherein the mammal consumes an egg or egg meal from one or more eggs of one or more chickens inoculated with Gkn-1, wherein an anti-Gkn-1 antibody or immunoglobulin is deposited in the egg as a result of inoculating the one or more chickens with Gkn-1, wherein the mammal does not have colitis, and wherein the anti-Gkn-1 antibody or immunoglobulin binds to and neutralizes the Gkn-1 inside the mammal, thereby promoting weight loss in the mammal.

* * * * *

SEQUENCE LISTING

<160> NUMBER OF SEQ ID NOS: 1

<210> SEQ ID NO 1
<211> LENGTH: 21
<212> TYPE: PRT
<213> ORGANISM: Artificial
<220> FEATURE:
<223> OTHER INFORMATION: Synthetic

<400> SEQUENCE: 1

-continued

```
Leu Asp Ala Leu Val Lys Glu Lys Lys Leu Gln Gly Lys Gly Pro Gly
1               5                   10                  15

Gly Pro Pro Pro Lys
            20
```